(12) United States Patent
Lien

(10) Patent No.: US 8,684,226 B2
(45) Date of Patent: Apr. 1, 2014

(54) GLOVE DISPENSING ASSEMBLY

(75) Inventor: Khoa T. Lien, Milton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/976,525

(22) Filed: Dec. 22, 2010

(65) Prior Publication Data
US 2012/0160865 A1 Jun. 28, 2012

(51) Int. Cl.
*B65D 83/08* (2006.01)
*B65G 59/02* (2006.01)

(52) U.S. Cl.
USPC .............................. 221/45; 221/61; 221/306

(58) Field of Classification Search
USPC ................... 221/45, 47, 48, 51, 302
See application file for complete search history.

(56) References Cited

U.S. PATENT DOCUMENTS

| | | | | |
|---|---|---|---|---|
| 3,384,083 A | * | 5/1968 | Cozza et al. | 604/292 |
| 5,622,281 A | * | 4/1997 | Annand | 221/48 |
| 5,649,336 A | * | 7/1997 | Finch et al. | 15/104.94 |
| 5,816,440 A | * | 10/1998 | Shields et al. | 221/45 |
| 6,349,849 B1 | * | 2/2002 | Pehr | 221/33 |
| 6,488,175 B2 | * | 12/2002 | Shiffler et al. | 221/47 |
| 6,715,633 B2 | | 4/2004 | Thoms | |
| 6,901,723 B2 | * | 6/2005 | Jordan et al. | 53/429 |
| 6,971,542 B2 | * | 12/2005 | Vogel et al. | 221/45 |
| 7,661,554 B2 | | 2/2010 | Szymonski et al. | |
| 2008/0277405 A1 | * | 11/2008 | Leach et al. | 221/1 |
| 2011/0062179 A1 | * | 3/2011 | Stollery et al. | 221/45 |

* cited by examiner

*Primary Examiner* — Gene Crawford
*Assistant Examiner* — Kelvin L Randall, Jr.
(74) *Attorney, Agent, or Firm* — Dority & Manning, P.A.

(57) ABSTRACT

A glove dispensing assembly includes a stack of interfolded gloves. In particular, the gloves are folded in an S-like arrangement including a first fold and a second fold. The finger portion of a leading glove is folded in between a cuff portion and an intermediate portion of a subsequent glove. The manner in which the gloves are folded allows for the gloves to be dispensed in a perpendicular direction or a lateral direction.

10 Claims, 5 Drawing Sheets

GLOVE DISPENSING ASSEMBLY

BACKGROUND

Elastic gloves made from natural latex polymers or from synthetic polymers are used in numerous applications. Such gloves, for instance, are used by medical personnel during examinations, surgeries and the like. Elastic gloves are also used during food preparation and in clean room environments. The gloves are used to protect the hands of a wearer and/or to prevent contamination.

The elastic gloves can be made from numerous materials. For instance, as described above, in one embodiment, the gloves are made from natural latex polymers. Synthetic polymers that are used to make elastic gloves include polyvinyl chloride, nitrile polymers, block copolymers such as styrene-ethylene butylene-styrene block copolymers, and the like.

Elastic gloves are commonly packaged together in dispensers that are intended to dispense the gloves one at a time. Such dispensers are very useful especially in environments where new gloves are constantly needed. For instance, physicians or nurses performing medical examinations and tests are constantly discarding old gloves and donning new gloves as they see new patients.

Problems have been experienced in the past, however, in designing dispensers that efficiently dispense gloves one at a time. Currently, gloves are packaged and stacked together in a dispenser such that the fingers of one glove are placed on top of the fingers of another glove and then folded in half to overlap one another. This arrangement allows for dispensing of the gloves cuff first by pulling the cuff of the leading glove in the stack in a motion perpendicular to the fold. Dispensing of the gloves, for instance, is typically achieved by a downward motion. The above configuration, however, has various limitations. For instance, due to the amount of overlap between the gloves, pulling one glove has a tendency to also pull an adjacent glove through the dispenser. If the second glove is not needed, users typically "stuff" the extra glove back into the dispenser creating further problems downstream.

Another problem with the above configuration is that the gloves can only be removed from the dispenser in a direction perpendicular to the fold which translates into either removing gloves only from the top or bottom of the dispenser.

SUMMARY

The present disclosure is generally directed to a glove dispensing assembly that is configured to dispense gloves one at a time. As will be described in greater detail below, the gloves are interfolded within the assembly in a manner that allows for the gloves to be dispensed from the stack in a perpendicular direction or in a lateral direction. The manner in which the gloves are interfolded is also very efficient in that once a glove is withdrawn, a subsequent glove is presented for subsequent use.

In one embodiment, for instance, the glove dispensing assembly comprises a stack of interfolded gloves. Each glove includes a finger end and a cuff end. The stack of interfolded gloves includes an initial glove and a plurality of subsequent gloves.

Each of the subsequent gloves includes a first fold and a second fold that divides the glove into three different portions, namely a cuff portion, an intermediate portion, and a finger portion. The cuff portion is folded along the first fold towards a first side of the intermediate portion, while the finger portion is folded along the second fold towards a second and opposite side of the intermediate portion. In this manner, the plurality of subsequent gloves are folded in an S-like manner.

In one embodiment, the finger portion of one glove is positioned in between an intermediate portion and a cuff portion of an adjacent glove in the stack. The cuff end of each glove in the stack can be oriented toward the initial glove such that the gloves are dispensed cuff end first. If desired, the arrangement can be reversed such that the gloves can be dispensed finger end first.

The glove dispensing assembly can further include a dispenser surrounding the stack of interfolded gloves. The dispenser can be made from, for instance, paperboard or from a polymer material. The dispenser can be reusable or disposable. The dispenser defines an opening through which the gloves are dispensed. As described above, the gloves are interfolded such that when a glove is pulled through the opening, a portion of a subsequent glove is also pulled through the opening and presented for subsequent use.

Of particular advantage, the gloves can be dispensed from the dispenser in a perpendicular direction or in a lateral direction. The perpendicular direction refers to the direction that is perpendicular to the direction in which the different portions of the glove are stacked. The lateral direction, on the other hand, refers to a direction that is parallel to the folded portions of the glove. Thus, once the gloves are loaded into the dispenser, the dispenser may dispense the gloves from the top, the bottom, or one of the sides.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
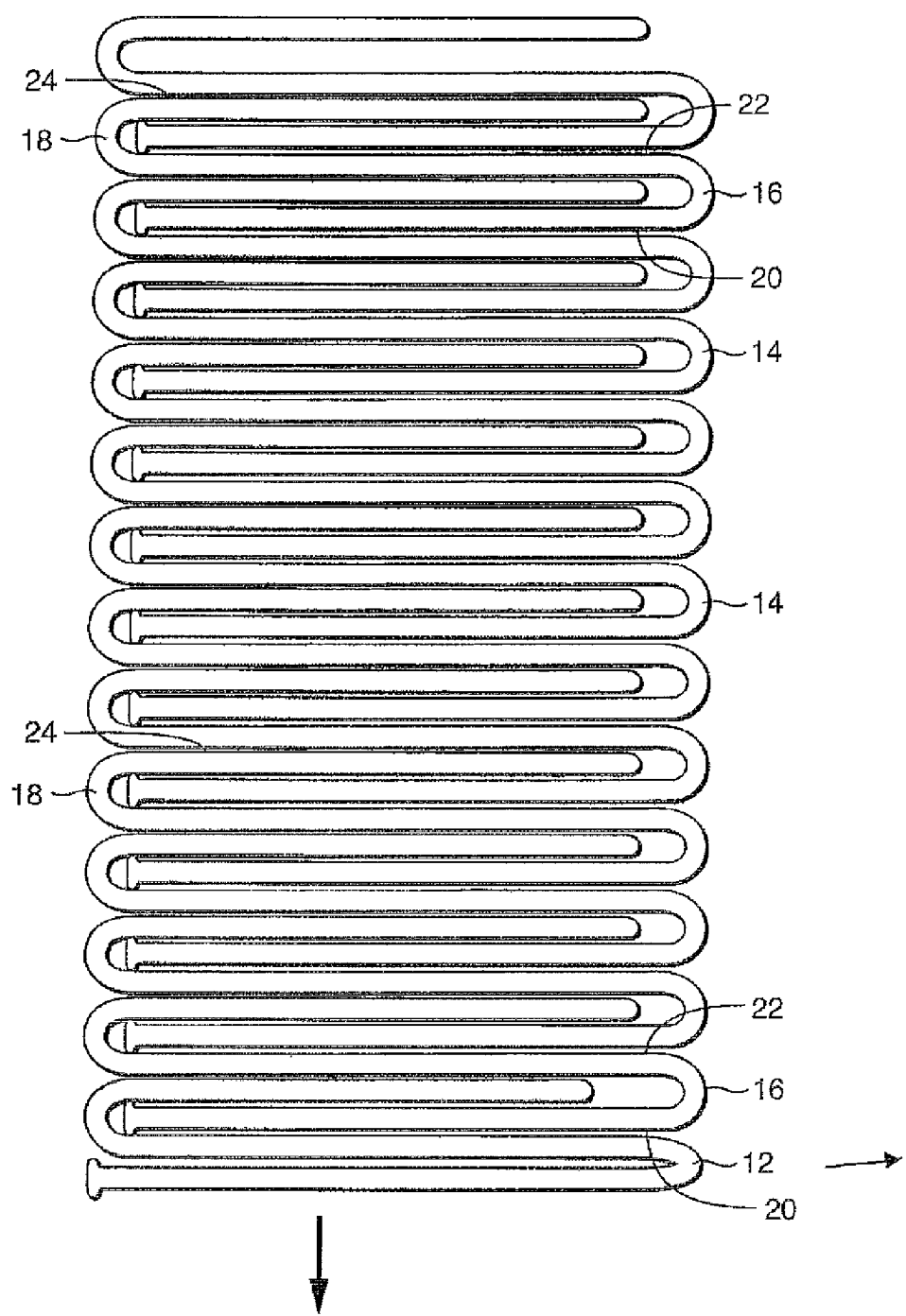
FIG. 1 is a side view of one embodiment of a glove dispensing assembly configured in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a glove dispensing assembly that includes a stack of interfolded gloves. The gloves are interfolded such that when placed in a dispenser, the gloves can be removed from the dispenser one at a time. More particularly, when one glove is removed from the dispenser, a portion of a subsequent glove is partially withdrawn from the dispenser as the first glove is removed. In this manner, the subsequent glove is presented for removal from the dispenser for subsequent use.

As will be described in greater detail below, the interfolded gloves contained in the dispensing assembly include two folds in an S-like configuration. The additional fold enables the gloves to be dispensed in a lateral direction to the glove fold or may be dispensed perpendicular to the glove fold. The double fold design also prevents against gloves being unintentionally removed from the stack. In particular, the double fold design prevents against two gloves being removed from the stack when a single glove is pulled upon.

The gloves that are contained in the glove dispensing assembly of the present disclosure can vary depending upon the particular application. The gloves can be made from any sheet-like material. The gloves, for instance, can be made from a woven fabric, a knitted fabric, or a nonwoven fabric. The gloves can also be made from a fabric laminate. In one particular embodiment, the gloves are made from an elastic material, such as an elastic polymer. For instance, the gloves can be made from a natural rubber latex polymer or from a synthetic polymer. Synthetic polymers that are used to produce gloves include polyvinyl chloride and other vinyl plastisols, neoprene, nitrile rubber, and the like. The elastic gloves can also be formed from a styrenic polymer and/or from a block copolymer. For instance, the gloves can be formed from a styrene-butylene-styrene polymer or a styrene-ethylene butylene-styrene polymer. In yet another embodiment, the gloves can be made from a styrene-isoprene-styrene polymer.

Referring to FIG. 1, one embodiment of a glove dispensing assembly generally 10 is shown. The assembly 10 includes a plurality of interfolded gloves. In particular, the assembly includes an initial glove 12 and a stack of subsequent gloves 14.

As shown, each of the subsequent gloves 14 includes a first fold 16 and a second fold 18. The folds 16 and 18 divide each glove into a cuff portion 20, an intermediate portion 22, and a finger portion 24. As shown, the cuff portion 20 is folded towards one side of the intermediate portion 22, while the finger portion 24 is folded towards an opposite side of the intermediate portion 22. In this manner, each of the subsequent gloves 14 are folded in an S-like configuration.

The stack of subsequent gloves 14 are also interfolded together. In particular, the finger portion 24 of a leading glove in the stack is positioned in between a cuff portion 20 and an intermediate portion 22 of a subsequent glove. In the embodiment illustrated in FIG. 1, the gloves are intended to be dispensed cuff-first. Thus, the gloves are stacked such that the cuff end of a glove is positioned downstream from a finger end. It should be understood, however, that the arrangement can be reversed such that the gloves are dispensed finger-first.

The initial glove 12 in the stack illustrated in FIG. 1 also includes a first fold and a second fold in an S-like arrangement. In particular, the finger portion of the initial glove 12 is positioned in between the cuff portion and the intermediate portion of a subsequent glove. The intermediate portion and the cuff portion of the initial glove 12 can be present in the stack in any suitable folded arrangement. In the embodiment illustrated, for instance, the cuff portion is folded directly onto the intermediate portion. In an alternative embodiment, however, the initial glove 12 may include only a single fold (especially if laterally dispensed) or may include more than two folds. For instance, the cuff portion of the initial glove may be folded twice so that the cuff end of the glove is located in the center of the stack which may facilitate perpendicular dispensing.

Not shown, the glove dispensing assembly 10 may include a final glove in the stack in which one portion of the glove is interfolded with a glove downstream. The final glove in the stack may also include only a single fold, may include two folds, or may include more than two folds.

Figure 2:
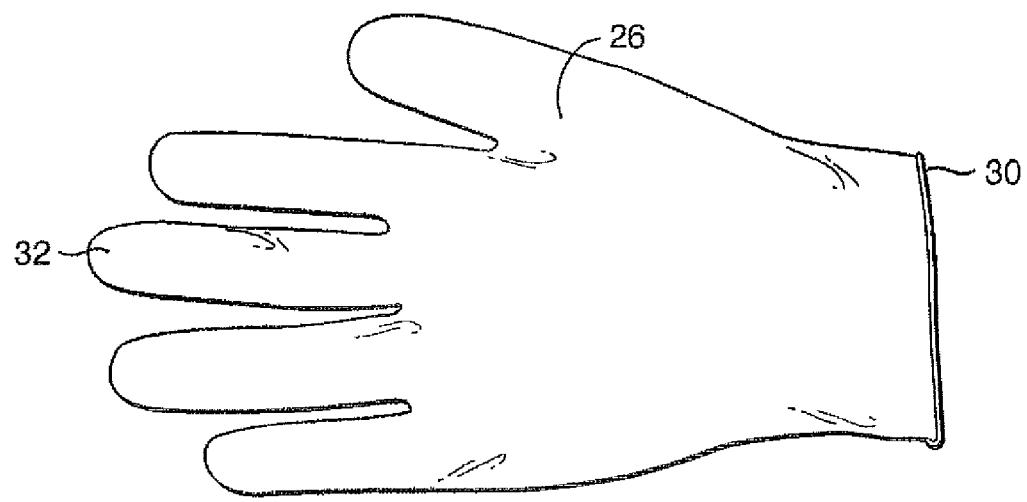
FIGS. 2 through 7 are perspective views that together represent one embodiment of a process for folding gloves together in accordance with the present disclosure.
Figure 3:
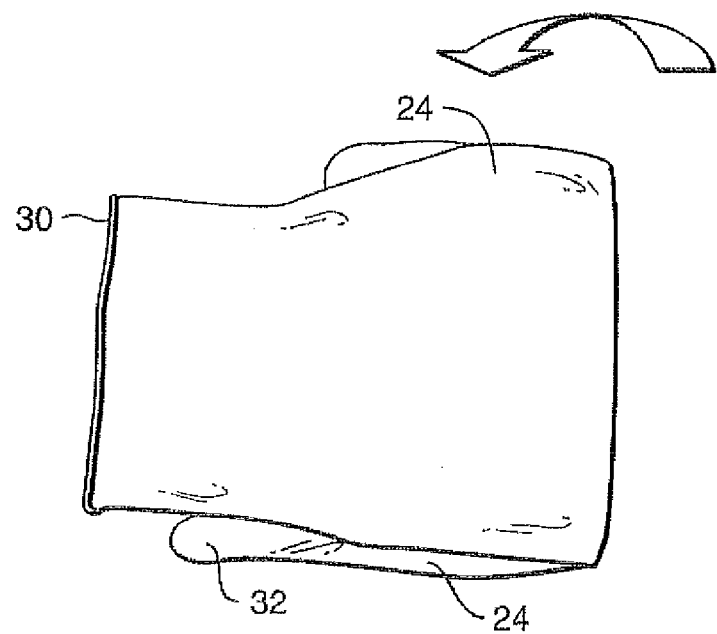

Referring to FIGS. 2 through 7, the manner in which gloves are interfolded in accordance with the present disclosure is shown. Referring to FIG. 1, for instance, a first glove 26 is illustrated. The first glove 26 includes a cuff end 30 and a finger end 32. As shown in FIG. 2, a first fold 16 is made in glove 26 by folding the cuff end 30 over the finger end 32. The first fold 16 forms the finger portion 24.

A second glove 28 is then placed over the first glove 26. More particularly, the second glove 28 includes a finger portion 124 which is placed in overlapping relationship on the first glove 26. The finger portion 124 is positioned on a side of the first glove 26 opposite the finger portion 24.

Figure 5:
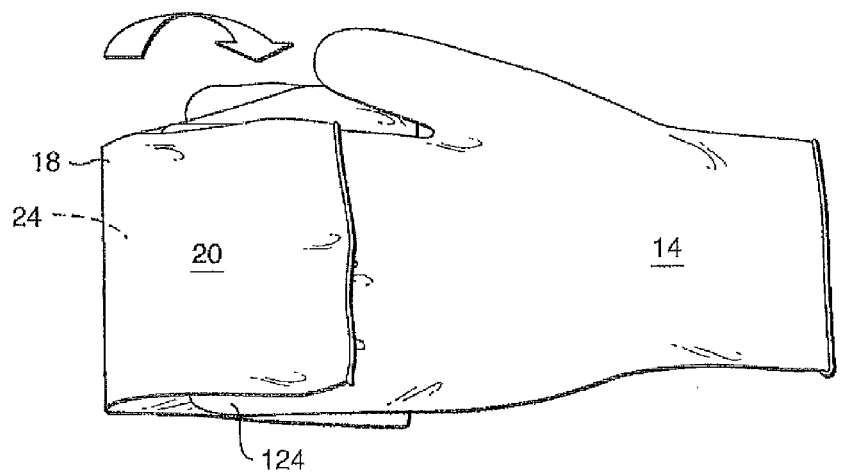

Referring to FIG. 5, the next step in the process is to form a second fold 18 in the first glove 26. As shown, the cuff portion 20 of the first glove 26 is folded back over the finger portion 124 of the second glove 28 along a second fold 18. In this manner, the first glove 26 assumes an S-like folded configuration in which an intermediate portion exists in between a finger portion 24 and a cuff portion 20.

Figure 4:
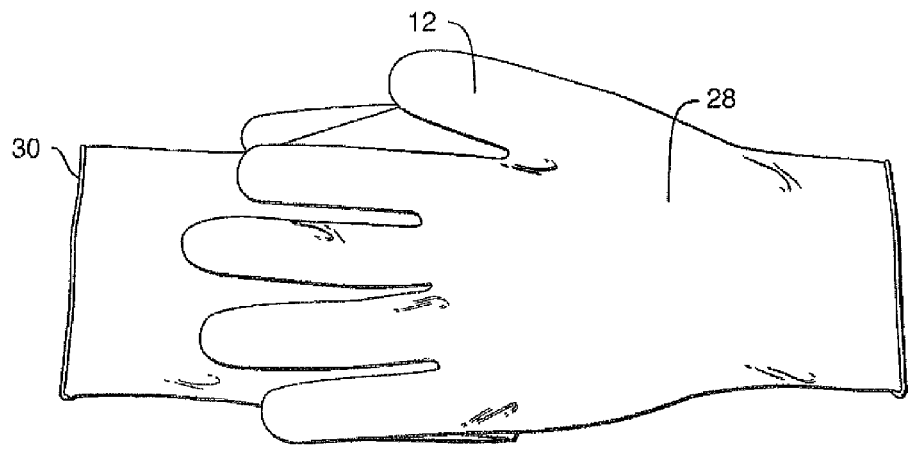
Figure 6:
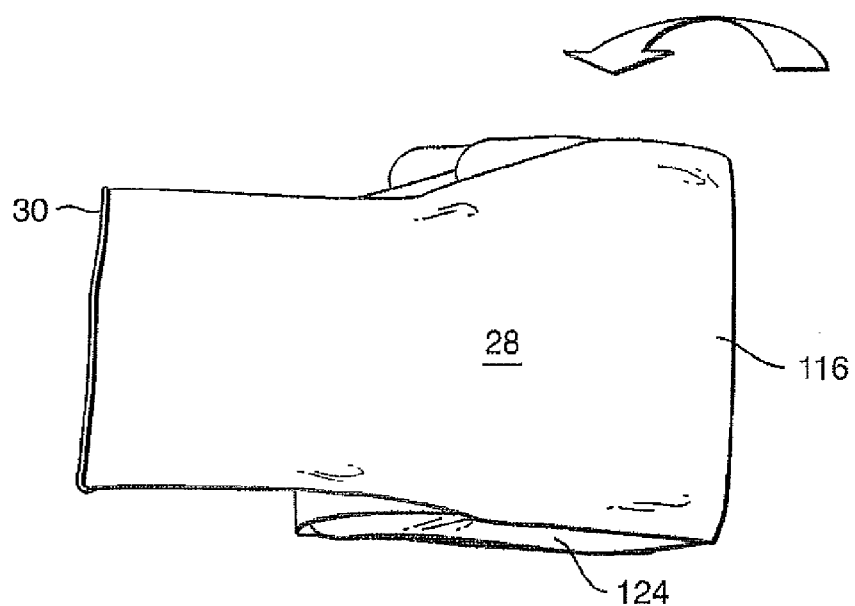
Figure 7:
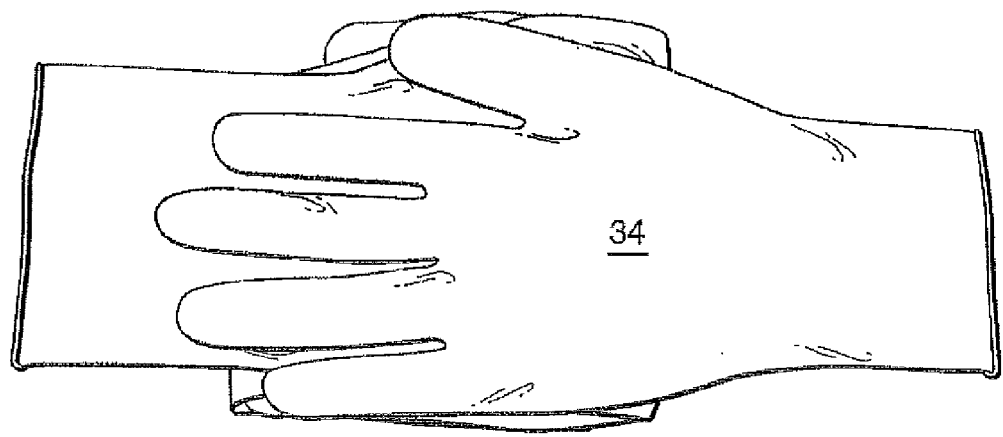

Referring now to FIG. 6, the second glove 28 is shown being folded along a first fold 116 over the cuff portion 20 of the first glove 26. The first fold 116 defines the finger portion 124. As shown in FIG. 7, the next step is to place a third glove 34 over the second glove 28. In particular, the finger portion of the third glove 34 is placed on an intermediate portion of the second glove 28. The process illustrated in FIGS. 4 through 6 are then repeated for each additional glove until an assembly is formed containing the desired number of gloves. In the process illustrated in FIGS. 2 through 7, the first glove 26 forms the final glove in the stack. The last glove to be added to the stack becomes the initial glove for dispensing. In the process shown, the gloves are dispensed cuff-first. As explained above, however, the configuration can be reversed such that the gloves are dispensed finger end first.

The number of gloves contained in any given assembly may vary depending upon various factors. In general, the assembly can contain from about 10 to about 500 gloves, such as from about 50 to about 200 gloves.

Figure 8:
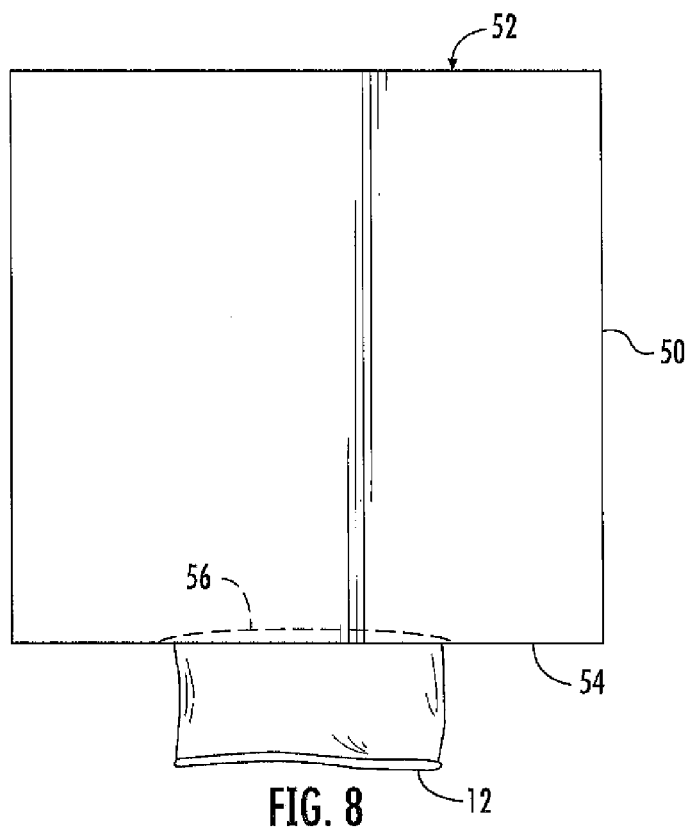
FIG. 8 is a perspective view of a glove dispenser made in accordance with the present disclosure.

The assembly of gloves as shown in FIG. 1 can be dispensed one at a time from any suitable dispenser. Referring to FIG. 8, for instance, one embodiment of a dispenser 50 is shown. As illustrated, the dispenser 50 includes a top 52 and a bottom 54. The bottom 54 defines an opening 56 through which the gloves are dispensed, such as initial glove 12. The dispenser 50 can be made from any suitable material. For instance, in one embodiment, the dispenser 50 can be disposable and made from paperboard. Alternatively, the dispenser 50 may be reusable and refillable and may be made from paperboard, a polymer, a metal, or any other suitable material.

In one embodiment, the dispenser 50 can be made from a paperboard material. The opening 56 can be initially covered by a removable panel. For instance, the removable panel may be defined by perforations made into the dispenser wall. In order to access the gloves, a user can remove the removable panel exposing the opening 56 for withdrawing the gloves from the dispenser.

In FIG. 8, the gloves are withdrawn from the dispenser through the bottom 54. In this manner, the gloves are removed from the dispenser in a direction perpendicular to the folds of the glove or, in other words, in a direction perpendicular to the folded cuff portion, intermediate portion, and finger portion as shown in FIG. 1. It should be understood that in addition to being dispensed from the bottom 54, the gloves may also be dispensed from the top 52.

Figure 9:
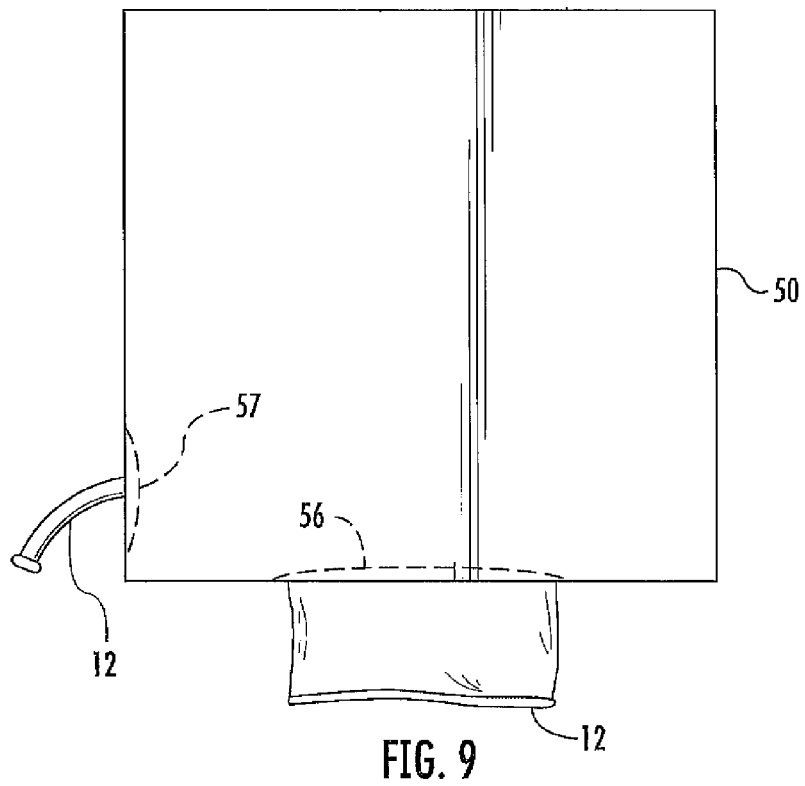
FIG. 9 is a perspective view of another embodiment of a glove dispenser made in accordance with the present disclosure.

Of particular advantage, in addition to dispensing the gloves in a perpendicular direction, the glove dispensing assembly of the present disclosure is also well suited to dispensing gloves in a lateral direction. As used herein, the lateral direction is the direction that is parallel to the cuff portion, the intermediate portion, and the finger portion of the folded gloves. As shown in FIG. 9, for instance, the stack of interfolded gloves may be contained within the dispenser 50. In this embodiment, the dispenser 50 includes an opening 57 that is located on one side of the dispenser. As shown, an initial glove 12 can be removed from the dispenser 50 causing a subsequent glove to be partially withdrawn through the opening 57 for later use. In the embodiment illustrated in FIG. 9, similar to the embodiment illustrated in FIG. 8, the opening 57 may initially be covered by a removable panel that is defined by perforations.

In one alternative embodiment of the present disclosure, the dispenser 50 may include a removable panel located on the bottom surface of the dispenser and a removable panel located on the side of the dispenser as shown in FIG. 9. In this manner, a user can decide later whether to dispense the gloves in a perpendicular direction or in a lateral direction.

The dispenser 50 illustrated in FIGS. 8 and 9 may also include a mounting device for mounting the dispenser on an adjacent surface. The mounting device, for instance, may comprise an adhesive that is initially covered by a release liner. Once the release liner is removed, the adhesive is exposed for attachment to a surface. In an alternative embodiment, the mounting device may comprise a frame that is mounted to a wall using an adhesive or using a mechanical fastener, such as a screw. The dispenser 50 may fit within the frame for dispensing the gloves.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A glove dispensing assembly comprising:
   a dispenser surrounding a stack of interfolded gloves, the dispenser defining an opening through which the gloves are dispensed;
   the stack of interfolded gloves made from an elastic material, the elastic material comprising a natural latex polymer, a polyvinyl chloride polymer, a nitrile polymer, a block copolymer, or a neoprene, each glove including a finger end comprising distinct and separate fingers and a cuff end, the stack including an initial glove and a plurality of subsequent gloves, wherein each of the subsequent gloves includes a first fold and a second fold defining a cuff portion, an intermediate portion and a finger portion, the cuff portion being folded towards a first side of the intermediate portion and the finger portion being folded towards a second and opposite side of the intermediate portion, wherein the finger portion of a subsequent glove is positioned in between an intermediate portion and a cuff portion of an adjacent glove in the stack and wherein the cuff end of each subsequent glove in the stack is oriented toward the initial glove in relation to the finger end of each subsequent glove such that the gloves are dispensed through the opening cuff end first, wherein the dispenser has an opening defined entirely within at least one side of the dispenser in a lateral direction in relation to the first fold and the second fold of each of the plurality of subsequent gloves, wherein the gloves are removed cuff first in a direction parallel to the gloves laying in the stack from the opening defined in the at least one side of the dispenser and a separate opening distanced from the opening in the at least one side and defined entirely within at least the top or bottom of the dispenser positioned in a perpendicular direction in relation to the first fold and the second fold of each of the plurality of subsequent gloves, wherein the gloves are removed cuff first in a direction perpendicular to the gloves laying in the stack from the opening defined within at least the top or bottom of the dispenser, wherein the plurality of subsequent gloves are each folded in an S-like configuration; and wherein a removable panel is associated with each opening, and removing either panel and pulling gloves through either opening maintains the interfolded nature of the entire stack within the assembly regardless of the quantity of gloves present in the stack.

2. A glove dispensing assembly as defined in claim 1, wherein the gloves are interfolded such that when a glove is pulled through the opening, a portion of a subsequent glove is also pulled through the opening.

3. A glove dispensing assembly as defined in claim 2, wherein the portion of the subsequent glove that is also pulled through the opening comprises the cuff portion of the glove.

4. A glove dispensing assembly as defined in claim 1, wherein the initial glove also includes a first fold and a second fold that divides the initial glove into a cuff portion, an intermediate portion and a finger portion.

5. A glove dispensing assembly as defined in claim 4, wherein the cuff portion of the initial glove is folded onto the intermediate portion of the initial glove and wherein the finger portion of the initial glove is interfolded with a subsequent glove.

6. A glove dispensing assembly as defined in claim 1, wherein the dispenser includes a top, a bottom, and at least one side, the opening being positioned on the bottom.

7. A glove dispensing assembly as defined in claim 1, wherein the opening is covered by a removable panel that is removed to access the stack of interfolded gloves.

8. A glove dispensing assembly as defined in claim 1, wherein the dispenser further includes a mounting device for mounting the dispenser to an adjacent surface.

9. A glove dispensing assembly as defined in claim 1, wherein the elastic material used to form the gloves comprises a film.

10. A glove dispensing assembly as defined in claim 9, wherein the elastic material used to form the gloves comprises a sheet-like film.

\* \* \* \* \*